(12) United States Patent
Rusche et al.

(10) Patent No.: US 6,365,593 B2
(45) Date of Patent: Apr. 2, 2002

(54) METHYLXANTHINES IN THE DIAGNOSIS AND TREATMENT OF AUTISTIC DISORDER

(75) Inventors: James R. Rusche, Framingham; Jundong Zhang, Newton, both of MA (US)

(73) Assignee: Repligen Corporation, Needham, MA (US)

( * ) Notice: Subject to any disclaimer, the term of this patent is extended or adjusted under 35 U.S.C. 154(b) by 0 days.

(21) Appl. No.: 09/834,169

(22) Filed: Apr. 12, 2001

Related U.S. Application Data

(60) Provisional application No. 60/196,423, filed on Apr. 12, 2000.

(51) Int. Cl.[7] .............................................. A61K 31/52
(52) U.S. Cl. ...................................................... 514/263
(58) Field of Search ......................................... 514/263

(56) References Cited

U.S. PATENT DOCUMENTS

| | | | | |
|---|---|---|---|---|
| 4,778,794 A | * | 10/1988 | Naruse et al. | ............... 514/254 |
| 5,008,251 A | * | 4/1991 | Gruber | ........................ 514/43 |
| 5,173,491 A | | 12/1992 | Kamoun et al. | ............. 514/265 |
| 5,686,311 A | | 11/1997 | Shaw | ........................... 436/86 |
| 6,020,310 A | * | 2/2000 | Beck et al. | .................... 514/12 |

FOREIGN PATENT DOCUMENTS

EP    0 646 009    8/1998

\* cited by examiner

*Primary Examiner*—Raymond Henley, III
(74) *Attorney, Agent, or Firm*—Fish & Richardson P.C.

(57) ABSTRACT

The invention is based on the discovery that the levels of one or more methylxanthines in urine samples are significantly decreased in children diagnosed with symptoms of autistic disorder, compared to the levels in normal children, and that levels of xanthines in urine are increased in autistic children. Consequently, the presence in the urine of levels of methylxanthines below a certain range and the level of xanthine above a certain range, are diagnostic of autistic disorder. In another aspect, one or more of these methylxanthines can be used to treat individuals exhibiting symptoms of autistic disorder.

18 Claims, 5 Drawing Sheets

7-Methylxanthine

3-Methylxanthine 3,7-Dimethylxanthine

METHYLXANTHINES IN THE DIAGNOSIS AND TREATMENT OF AUTISTIC DISORDER

CROSS REFERENCE TO RELATED APPLICATION

This application claims priority from U.S. Provisional Patent Application Serial No. 60/196,423 filed on Apr. 12, 2000, which is incorporated herein by reference in its entirety.

TECHNICAL FIELD

This invention relates to the diagnosis and treatment of autistic disorder.

BACKGROUND

Autistic disorder or autism is a severely debilitating developmental disorder characterized by a profound deficiency in verbal communication and normal socialization. Autism is typically diagnosed in children between the ages of two or three and six with a diagnosis usually being made based on behavioral symptoms using the guidelines in the Diagnostic and Statistical Manual of Mental Disorders (DSM)(American Psychiatric Association, Washington, D.C., pages 66–71, 1994). The fourth edition of these guidelines, DSM-IV, identifies autistic disorder as one of five separate disorders under the general category of Pervasive Developmental Disorders.

A child is diagnosed as having autistic disorder if the child fits into all of categories A, B, and C as follows (APA, 1994, p. 70–71):

A. A total of six (or more) items from (1), (2), and (3), with at least two from (1), and one each from (2) and (3):
  (1) qualitative impairment in social interaction, as manifested by at least two of the following: (a) marked impairment in the use of multiple nonverbal behaviors such as eye-to-eye gaze, facial expression, body postures, and gestures to regulate social interaction; (b) failure to develop peer relationships appropriate to developmental level; (c) a lack of spontaneous seeking to share enjoyment, interests, or achievements with other people (e.g., by a lack of showing, bringing, or pointing out objects of interest); and (d) lack of social or emotional reciprocity.
  (2) qualitative impairments in communication as manifested by at least one of the following: (a) delay in, or total lack of, the development of spoken language (not accompanied by an attempt to compensate through alternative modes of communication such as gesture or mime); (b) in individuals with adequate speech, marked impairment in the ability to initiate or sustain a conversation with others; (c) stereotyped and repetitive use of language or idiosyncratic language; and (d) lack of varied, spontaneous make-believe play or social imitative play appropriate to developmental level.
  (3) restricted repetitive and stereotyped patterns of behavior, interests, and activities, as manifested by at least one of the following: (a) encompassing preoccupation with one or more stereotyped and restricted patterns of interest that is abnormal either in intensity or focus; (b) apparently inflexible adherence to specific, nonfunctional routines or rituals; (c) stereotyped and repetitive motor mannerisms (e.g., hand or finger flapping or twisting, or complex whole-body movements); and (d) persistent preoccupation with parts of objects.

B. Delays or abnormal functioning in at least one of the following areas, with onset prior to age 3 years:
  (1) social interaction,
  (2) language as used in social communication, or
  (3) symbolic or imaginative play.

C. The disturbance is not better accounted for by Rett's Disorder or Childhood Disintegrative Disorder.

Although useful, diagnoses based on behavioral symptoms are necessarily subjective.

Once a patient is properly diagnosed, he or she can be treated using any of a variety of different treatments for autism that are currently available. Many of the treatments, however, address the symptoms of the disease, rather than the causes. For example, therapies ranging from psychoanalysis to psychopharmacology have been employed in the treatment of autism. Although some clinical symptoms may be lessened by these treatments, modest improvement, at best, has been demonstrated in a minor fraction of the cases. On the other hand, some therapies provide significant improvement in certain autistic individuals. For example, one recently discovered therapy for autism is the use of secretin as described in WO/US 98/52593, WO/US 99/13061, U.S. Pat. No. 6,020,310, and U.S. Pat. No. 6,197,746. Absent therapy, only a small percentage of autistic persons become able to function as self-sufficient adults.

SUMMARY

The invention is based on the discovery that the levels of one or more methylxanthines, such as 7-methylxanthine, in the urine of children diagnosed with autistic disorder are significantly decreased compared to the levels in normal children. In addition, the levels of xanthines are increased in children with autistic disorder.

In particular, 7-methylxanthine (7-MX) is present in a certain range in the urine of normal children, and the level of this metabolite is significantly decreased in individuals diagnosed with autistic disorder of the same age group. Consequently, the presence in the urine of levels of this metabolite below a certain range is diagnostic of autistic disorder. On the other hand, levels of xanthines are increased in autistic children, and thus, an increased level of a xanthine in an unknown urine sample indicates the likelihood of autistic disorder.

Based on these findings, the invention features a method of diagnosing an individual for an autistic disorder by obtaining a sample of urine from the individual; measuring a level of a methylxanthine (MX) in the urine sample; and comparing the level to a normal control or to a threshold level; wherein a level below the normal control or below a threshold level of about 5.3 micrograms of methylxanthine/ml of urine indicates a possibility of autistic disorder. In this method, an MX level below about 3.4 micrograms of methylxanthine/ml of urine indicates a strong likelihood that the individual has an autistic disorder, and an MX level above about 5.3 micrograms of methylxanthine/ml of urine indicates a strong likelihood that the individual does not have an autistic disorder.

In this method, the normal control can be from an individual or group of individuals who are the same age as the individual being diagnosed, and who do not have any diagnosed symptoms of autistic disorder.

In another aspect, the invention features a method of treating an individual exhibiting one or more symptoms of autistic disorder by administering to the individual an amount of a methylxanthine composition effective to inhibit one or more of the symptoms. In some embodiments, an effective amount of the methylxanthine composition can provide a urine concentration of at least about 5.0 micrograms of methylxanthine/ml of urine. The methylxanthine composition can comprise 7-methylxanthine, a dimethylxanthine, e.g., 1,3 or 3,7 dimethylxanthine, or a trimethylxanthine, such as 1,3,7-trimethylxanthine. The composition can also include one or more of caffeine, theobromine, and theophylline. The methylxanthine can be administered in a variety of ways, e.g., orally or intravenously. The composition can be administered at least once per day or at least once per week, depending, inter alia, on the individual being treated and the severity of symptoms.

In yet another aspect, the invention features another method of diagnosing an individual for an autistic disorder by obtaining a sample of urine from the individual; measuring a level of a xanthine in the urine sample; and comparing the level to a normal control; wherein a level above the normal control indicates a likelihood that the individual has an autistic disorder. In this method, the level of xanthine in the individual who is diagnosed as having symptoms of autistic disorder scan be two or three times the level of the normal control.

A methylxanthine composition is either purified methylxanthine, a compound or product that contains methylxanthine, a compound that increases the level of methylxanthine in the patient, or a compound or molecule that mimics the biological function of methylxanthine. Such a compound can be a methylxanthine precursor or prodrug, which is processed, e.g., metabolized, degraded, or cleaved, in the body to form methylxanthine. Examples include caffeine (1,3,7-trimethylxanthine), theobromine (3,7-dimethylxanthine), and theophylline (1,3-dimethylxanthine). Such a compound can also be a methylxanthine derivative, which includes methylxanthines, and other molecules or compounds bound (e.g., covalently or non-covalently) to methylxanthine, but that do not impair methylxanthine's biological activity in patients. Such compounds can also be methylxanthine mimetics, such as other small molecules that have a sufficiently similar three-dimensional shape or electron configuration that the molecule has at least 50 percent of the biological activity of methylxanthine. Such compounds can also be drugs or other compounds that induce the body to produce methylxanthine.

Methylxanthine compositions also include encapsulated methylxanthine, e.g., liposome- or polymer-encapsulated methylxanthine. Methylxanthine compositions also include methylxanthine linked (e.g., covalently or non-covalently) to various antibodies, ligands, or other targeting and enveloping or shielding agents (e.g., albumin or dextrose), to allow the methylxanthine to reach the target site (e.g., the central nervous system, muscle cells, or the peripheral nervous system) prior to being removed from the blood stream, e.g., by the kidneys and liver, and prior to being degraded.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
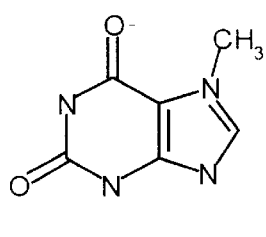
FIG. 1 is a representation of three different methylxanthines (MX).
Figure 1:
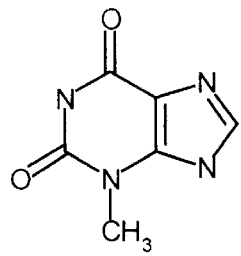
Figure 1:
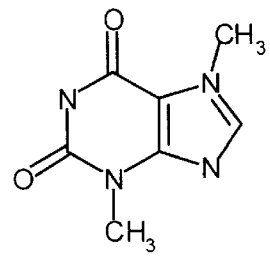

The invention is based on the finding that the levels of one or more methylxanthines, such as 7-methylxanthine, in the urine of children diagnosed with autistic disorder are decreased compared to the levels in normal children, whereas levels of xanthine are increased. For example, 7-methylxanthine (7-MX) is present in a range of about 3.4 to about 17.8 micrograms/ml in the urine of normal children, and the level of this metabolite is significantly decreased to a range of 0.0 to about 5.3 micrograms/ml of urine in individuals of the same age group diagnosed with symptoms of autistic disorder. Consequently, the presence in the urine of levels of this metabolite below 5.3 micrograms/ml indicates a likelihood that the individual has autistic disorder.

Methylxanthines in urine have been studied as metabolites of caffeine (1,3,7-trimethylxanthine), theophylline (1,3- dimethylxanthine), and theobromine (3,7-dimethylxanthine) (Denaro et al., Clin. Pharm. Therap., 59:284, 1996, which is incorporated herein by reference in its entirety). In humans, N3-demethylation of caffeine to form paraxanthine (1,7-dimethylxanthine), N1-demethylation to form theobromine, and N-7-demethylation to form theophylline, account, on average, for 80%, 11%, and 4%, respectively, of caffeine metabolism in vivo. Dimethylxanthines can be demethylated again to form methylxanthines. Furthermore, xanthines methylated at various degrees might be oxidized to uric acid by xanthine oxidase. Because N3-demethylation is the predominant pathway in man, it has been consistently reported that 1-MU, 1-MX, 1,7-DMU, and 1,7-DMX made up the major metabolites of caffeine, with lesser amount of 7-MX, 3-MX, 1,3-DMU, 3,7-DMX, and 1,3-DMX. Contrary to what was found in the literature, in the present study, the most abundant species are 7-MX, 3-MX, and 3,7-DMX at a ratio of roughly 1:0.6:1, suggesting the investigated methylxanthine may be generated by another metabolic pathway.

Theoretically, methylxanthines can be generated in two ways: (i) demethylation of caffeine or related tri- and dimethylxanthines, and (i) methylation of xanthine. It was confirmed that dimethylxanthines can be methylated in neonates to caffeine and there is evidence that the same reaction occurs in adults too. Presumably the enzyme that is responsible for the methylation of dimethylxanthines or similar enzymes can methylate xanthine. If the assumption that methylxanthines are generated by methylation of xanthine is true, then the changes in the source of xanthine, the source of the methyl group donor, and the activity of the methylation enzyme will affect the concentration of methylxanthines.

In addition to providing a diagnostic method, methylxanthines can also be used to treat symptoms of autistic disorder. In particular, a hormone, secretin, has been shown to improve symptoms of individuals diagnosed with autistic disorder. See, e.g., U.S. Pat. Nos. 6,020,310 and 6,197,746, which are incorporated herein by reference in their entirety. As a result of the stimulated secretion of pancreatic bicarbonate fluid by secretin, the absorption of some factors that participate in the metabolic production of methylxanthines might be improved. In addition, methylxanthines are known for their affinity to adenosine receptors that are widely distributed in the brain. Based on the findings described herein, and the facts noted above, methylxanthine compositions, as defined herein, for example, methylxanthines themselves, or compounds that are involved in the generation of xanthines, can be administered to autistic individuals, e.g., such as children, to improve one or more of their symptoms of autistic disorder.

General Methods of Diagnosis

Urine samples from individuals, e.g., children, suspected of having autistic disorder are collected in 50 ml polypropylene centrifuge tubes and stored at a temperature below freezing, e.g., at −20° C. The samples are later thawed and centrifuged before pre-purification by solid phase extraction using e.g., SEP-PAK™ columns. The following is a suitable protocol for SEP-PAK™ extraction of one urine sample:

spin urine samples at 1500 rpm for 10 minutes;

decant ~5 ml into a fresh 15 ml conical tube, and add 1.6 µl of concentrated HCl/ml urine to acidify the urine;

pre-wash SEP-PAK with 5 ml MeOH;

equilibrate with 10 ml 0.1% HOAc/RO $H_2O$;

load 2 ml of acidified urine;

wash with 10 ml 0.1% HOAc/2% NaCl;

elute with 2 ml 80% MeOH/20% [0.1% HOAc/$H_2O$]; and add 1 ml of 50 mM ammonium bicarbonate (pH 7.7) to the eluent to neutralize for storage.

A fresh syringe should be used for each buffer, and each urine sample.

Suitable HPLC conditions to detect and analyze the methylxanthines and xanthines in a urine sample are as follows:

A buffer: 0.05% TFA/$H_2O$ pH 2.6 w/$NH_4OH$

B buffer: 0.05% TFA/ACN

YMC column ODS-AQ C18 4.6×150 mm (SN#041521020)

The following gradient can be used:

| Time | % B |
| --- | --- |
| 3 | 5 |
| 38 | 40 |
| 43 | 40 |
| 45 | 90 |
| 49 | 90 |
| 51 | 5 |
| 57 | 5 |

Samples are normalized for urinary output and variations in dilution using a standard creatinine assay. A portion of each sample is assayed to determine the creatinine content. Each sample is then diluted with water to achieve a standard creatinine concentration of 250 mmol in 100 µl of the sample.

Once the urine samples are properly pretreated, the level of methylxanthine, e.g., 7-MX, or xanthine is determined. This can be done as described herein, or by using any standard method of detecting methylxanthines and xanthines, such as HPLC. Each sample can be injected into the HPLC two times to assure accuracy.

Based on the information described herein, the level of methylxanthine in each sample is compared either to a control from one or more normal individuals of the same age or age group, or the level in the sample is compared to the following threshold values. The level of 7-MX in children with autistic disorder ranges from 0.0 to 5.3 micrograms/ml of urine, whereas the level of 7-MX in normal children ranges from 3.4 to 17.8 micrograms/ml of urine. As a result, a sample having a 7-MX level less than 3.4 micrograms/ml indicates a high likelihood of autistic disorder, whereas a sample having a 7-MX level greater than 5.3 micrograms/ml indicates a low likelihood of autistic disorder. A sample in the range of 3.4 to 5.3 micrograms/ml of 7-MX indicates a possibility or likelihood of autistic disorder and should be repeated and optionally confirmed using other standard diagnostic tests.

In addition, a level of xanthine that is higher than a comparable control, e.g., 2, 3, or 3.5 times higher, indicates the likelihood of autistic disorder.

General Methods of Therapy

Methylxanthine compositions can be used to treat individuals exhibiting symptoms of autistic disorder. The methylxanthine compositions, e.g., 7-MX, can be formulated according to standard techniques and administered using a variety of known routes of administration.

To formulate the therapeutic methylxanthine compositions, the methylxanthines can be further purified by standard methods to remove contaminants, if present. The final compositions can be lyophilized and resuspended in sterile, deionized water before further compounding. The therapeutic compositions can be formulated as solutions, suspensions, suppositories, tablets, granules, powders, capsules, ointments, or creams. In the preparation of these compositions, at least one pharmaceutical excipient can be included. Examples of pharmaceutical excipients include solvents (e.g., water or physiological saline), solubilizing agents (e.g., ethanol, polysorbates, or Cremophor EL7), agents for achieving isotonicity, preservatives, antioxidizing agents, lactose, starch, crystalline cellulose, mannitol, maltose, calcium hydrogen phosphate, light silicic acid anhydride, calcium carbonate, binders (e.g., starch, polyvinylpyrrolidone, hydroxypropyl cellulose, ethyl cellulose, carboxy methyl cellulose, or gum arabic), lubricants (e.g., magnesium stearate, talc, or hardened oils), or stabilizers (e.g., lactose, mannitol, maltose, polysorbates, macrogols, or polyoxyethylene hardened castor oils). If desired, glycerin, dimethylacetamide, 70% sodium lactate, surfactant, or basic substances such as sodium hydroxide, ethylenediamine, ethanolamine, sodium bicarbonate, arginine, meglumine, or trisaminomethane can be added.

Biodegradable polymers such as poly-D,L-lactide-co-glycolide or polyglycolide can be used as a bulk matrix if slow release of the composition is desired (see e.g., U.S. Pat. Nos. 5,417,986, 4,675,381, and 4,450,150). Pharmaceutical preparations such as solutions, tablets, granules or capsules can be formed with these components. If the composition is to be administered orally, flavorings and/or colors can be added. Methods for formulating such preparations are well known in the art and can be found in, for example, "Remington's Pharmaceutical Sciences."

Although caffeine, theobromine, and theophylline and other methylxanthine precursors are often ingested, the new methylxanthine compositions can be administered via any appropriate route, e.g., intravenously, intraarterially, topically, orally, ocularly, by injection, intraperitoneally, intrapleurally, subcutaneously, intramuscularly, sublingually, nasally, by inhalation, intraepidermally, or rectally, using standard techniques. Additional di- and tri-methylxanthine compositions include various salts such as theocalcin, calcium diuretin, theosol, theosalin, theocal, theosodate, and agurin, as well as compounds such as Adisne, theamin, oxyphyllin, theocin soluble, and biophylline.

Dosages administered in practicing the invention will depend on factors including the specific methylxanthine used and its concentration in the composition, the mode, frequency, and time of administration, the age, weight, sex, body surface area, and general health of the subject, any other drugs being administered concurrently, and the severity of the autistic symptoms. Suitable dosages can be determined by one skilled in the art. In general, the new compositions can be administered in amounts ranging between 0.05 mg and 50 mg of the methylxanthine per kilogram of body weight, e.g., 0.1 to 10 mg/kg or 1.0 to 5.0 mg/kg. The dosage should be adjusted to provide a urine level of at least about 5 micrograms, and up to about 10, 15, or 20 micrograms, of methylxanthine/ml of urine. This level can be easily determined empirically, and the dosage administered can be slowly increased over a period of days to achieve the desired urine level. Once the proper urine level is achieved, it can be easily maintained over time as required. The dosage range for veterinary use can be adjusted according to body weight.

Administration is repeated as necessary, as determined by one skilled in the art. By varying the amount of the composition, the administration protocol can be optimized for eliciting a maximal improvement in symptoms of autistic disorder. Physicians, pharmacologists, and other skilled artisans are able to determine the most therapeutically effective treatment regimen, which will vary from patient to patient. The potency of a specific composition and its duration of action can require administration on an infrequent basis, including administration in an implant made from a polymer that allows slow release of the methylxanthines.

Skilled artisans are also aware that the treatment regimen must be commensurate with issues of safety and possible toxic effect produced by the methylxanthines or other components in the compositions. As a result, before administering the above compositions to humans, toxicity testing can be determined by standard pharmaceutical procedures, using either cells in culture or experimental animals to determine the $LD_{50}$ (the dose lethal to 50% of the population). In an example of toxicity testing, the methylxanthine compositions can be administered to mice via an oral or parenteral route with varying dosages of methylxanthine in the composition, and the mice observed for signs of toxicity using standard techniques.

EXAMPLES

The invention is further described in the following examples, which do not limit the scope of the invention described in the claims.

Example 1

Metabolite Differences in the Urines of Non-Autistic and Autistic Individuals

Samples of urine from autistic and non-autistic subjects were collected and analyzed for the presence of various metabolites before and after secretin treatment. Urine samples were analyzed by HPLC with a 4.5×100 mm C18 column detected at 215 nm and 280 nm. A peak at retention time of 5.5 minutes (RT5.5) was found to increase in size after secretin treatment in some children. It was also noticed that there are two other peaks at RT6.2 and RT9.8 whose UV scans are very much like RT5.5. The size of RT6.2 and RT9.8 were also increased after secretin treatment. This initial observation was confirmed by analyzing more data on concentrations of RT5.5 and RT5.5-like peaks of non-autistic samples, autistic samples before secretin treatment and autistic samples after secretin treatment. RT5.5 and RT5.5-like peaks were then isolated and structurally identified as described herein.

Example 2

Characterization of Unknown Metabolites 500 ml urine samples were concentrated to 50 ml by lyophilization. The 50 ml concentrated sample was centrifuged and pre-purified by a SEP-PAK™ column. 10 ml sample was loaded onto one Sep-Pak column, washed with 10 ml 1% acetic acid in water and eluted with 20% methanol 1% acetic acid. The elution was pooled and concentrated to 5 ml under vacuum for HPLC injection. A Vydac 10×75 mm C18 column was used. The collections corresponding to peaks RT5.5, RT6.2, and RT9.8 were purified for several rounds until they were pure.

About 2 mg of pure RT5.5 was first generated and therefore the structure of RT5.5 was most extensively studied. The molecular ion of RT5.5 generated from ESI-MS is 167.1, suggesting its molecular weight is 166 with an even number of nitrogens. The molecular weight is confirmed by EI-MS to be 166. 1 HNMR of RT5.5 in deuterium water showed two single peaks at 7.91 ppm and 3.97 ppm with a ratio of 1:3, suggesting RT5.5 has one aromatic hydrogen and one methyl group. The small number of hydrogens in RT5.5 indicated that the structure of RT5.5 might be heavily substituted by heteroatoms, like O or N. By searching an NMR database of small chemicals, RT5.5's NMR spectrum matched the ones of N-methylxanthines. RT5.5 is further confirmed by HRMS that it is an N-methylxanthine. The calculated molecular weight of N-methylxanthine ($C_6H_6N_4O_2$) is 166.0491, the found molecular weight of RT5.5 is 166.0508 with an error of only 0.0017 Dalton units.

There are three possible N-methylxanthines, 1-methylxanthine (1-MX), 3-methylxanthine (3-MX), and 7-methylxanthine (7-MX). By matching with standards by retention time and UV scan, RT5.5 is found to be 7-methylxanthine. Furthermore, the fragmentation pattern of RT5.5 with EI-MS matched the structure of 7-methylxantine (see FIG. 1).

As in the peak RT5.5, the molecular ion of peak RT6.2 generated by ESI-MS is 167.1, suggesting RT5.5 and RT6.2 have the same molecular weight and might be isomers, such as different methylxanthines. $^{1H}$NMR of RT6.2 in deuterium water showed two single peaks at 8.11 ppm and 3.60 ppm with a ratio of 0.15:3. If one assumes that 3.60 ppm is one methyl group, 8.11 ppm hydrogen ought to be exchangeable with deuterium water to give a ratio of less than 1. By matching with standards by retention time and UV scan, RT6.2 is found to be 3-methylxanthine (3-MX). RT9.8 matched exactly by retention time and UV scan with 3,7-dimethylxanthine (3,7-DMX).

Example 3

Sample Analysis

Figure 2:
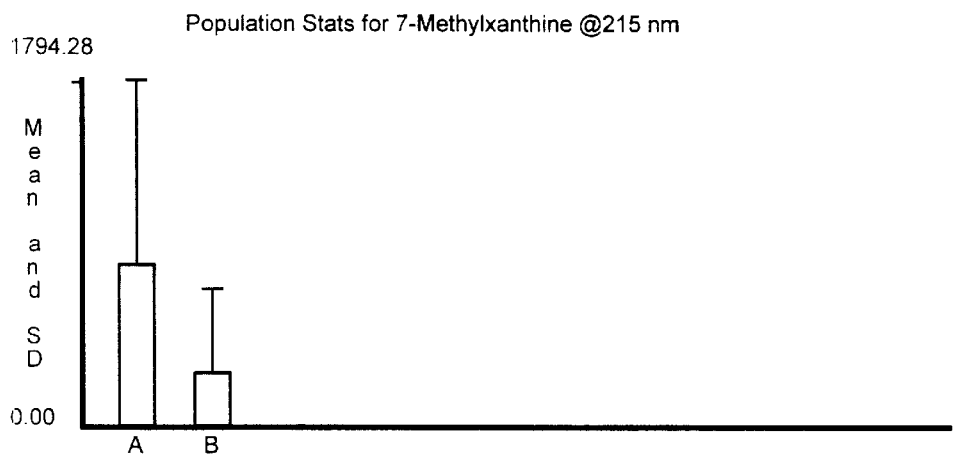
FIG. 2 is a graph showing the mean urine levels of 7-MX in normal and autistic individuals.

The peak areas at 215 nm of RT5.5 (7-Methyxanthine, 7-MX) of 13 non-autistic subjects and 39 autistic subjects were collected. Statistic analysis of the raw data for the non-autistic autistic group gave a mean of 846 (area under curve, AUC) with a standard deviation of 948, while the mean for the autistic group was 279 with a standard deviation of 442 (see FIG. 2, in which A is the non-autistic group, B is the autistic group). The two-tailed P value of the two groups of data is 0.0103, considered significant.

Figure 3:
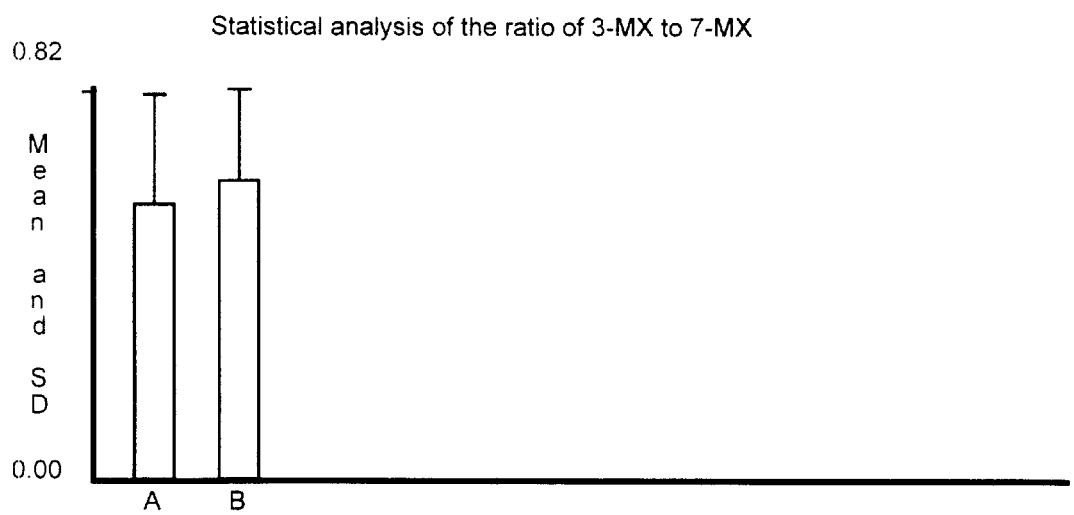
FIG. 3 is a graph showing the ratio of 3-MX to 7-MX in normal and autistic individuals.
Figure 4:
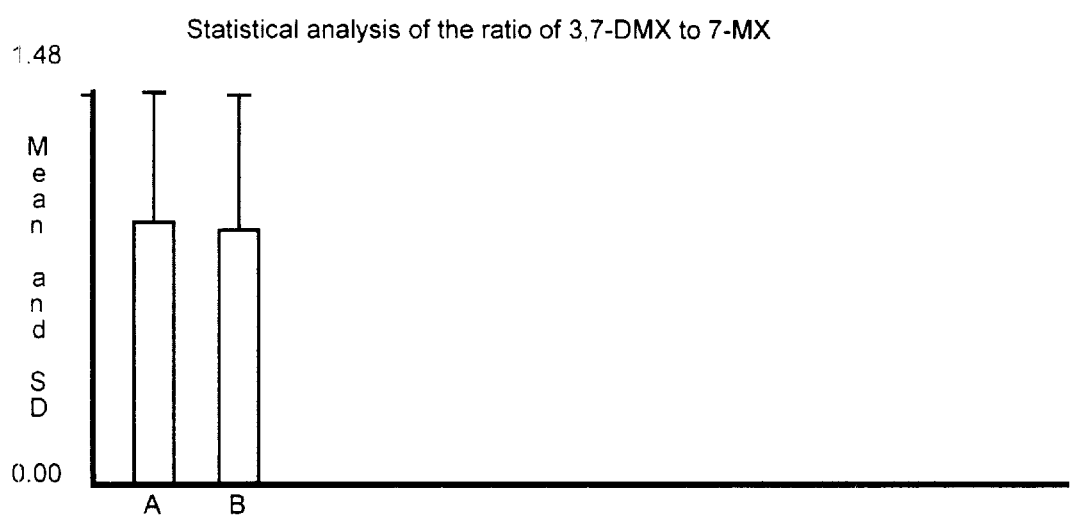
FIG. 4 is a graph showing the ratio of 3,7-dimethylxanthine (3,7-DMX) to 7-MX in normal and autistic individuals.

As shown in FIGS. 3 and 4, the ratio between 7-MX, 3-MX, and 3,7-DMX in the autistic group and the non-autistic group are the same statistically. Again, in these figures, A is the autistic group, B is the non-autistic group.

For the ratio of 3-MX to 7-MX, the mean of the autistic group (n=5) is 0.58 and the mean of the non-autistic group (n=1) is 0.64. The P value of the two sets of data is 0.66, considered not significant. Similarly, the ratio of 3,7-DMX to 7-MX for the autistic group (n=6) is 0.99 and the ratio for the non-autistic group (n=10) is 0.96. The P value is 0.92, considered not significant. Therefore, a concentration of one of the methylxanthines can be used as a measure of the total concentration of methylxanthines. The absorption ratio of the same amount of 7-MX, 3-MX, and 3,7-MX at 215 nm is determined to be 1:0.9:1.2, very close to the ratio of one.

Figure 5:
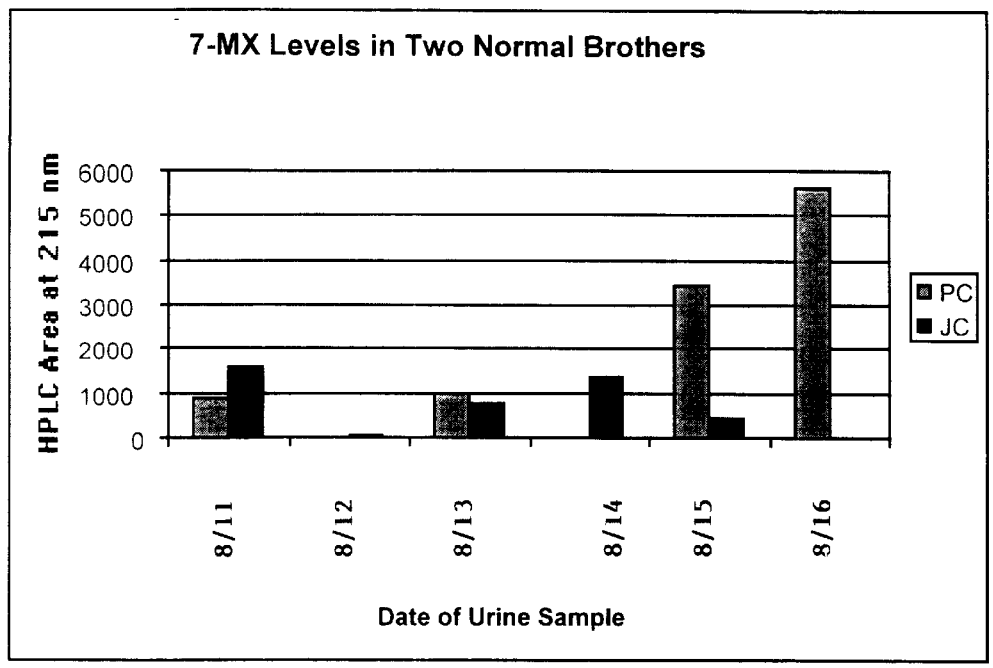
FIG. 5 is a graph showing the urine levels of 7-MX in two normal brothers.

The level of 7-MX in the first morning urine can vary greatly day by day. FIG. 5 is a graph showing the 7-MX levels of two non-autistic brothers. The variation of 7-MX may be a result of dietary changes. As a result, it is important to have test subjects and control subjects under the same diet, for at least 12 hours, and preferably 24 hours or more, prior to sampling of the urine. The 7-MX levels are comparable in samples on four of six days when both brothers' urines were sampled.

Example 4

Figure 6:
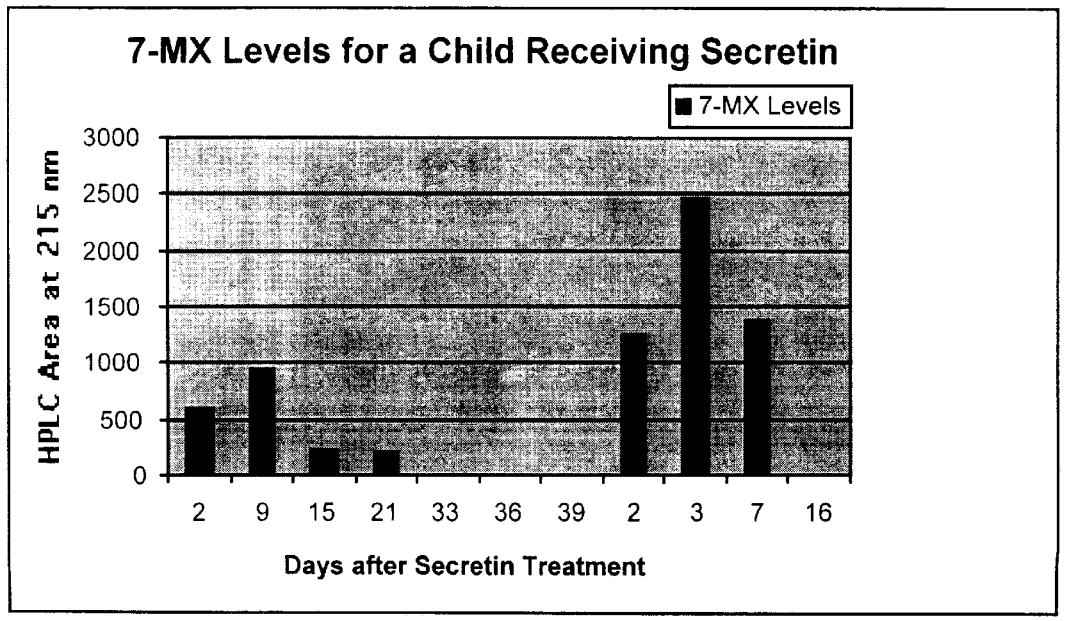
FIG. 6 is a graph showing the urine levels of 7-MX in an autistic child receiving secretin.

Effect of Secretin Treatment on the Urinary Production of 7-Methylxanthine in Austism The 7-MX levels in the first morning urine of autistic subjects after secretin treatment were monitored. One such child's 7-MX levels after two consecutive secretin infusion are shown in FIG. 6. The increase of 7-MX levels correlates with the treatment by secretin. The 7-MX level increases during the first week after secretin infusion and then decreases. The first treatment was with about 4 $\mu$g of secretin and the second treatment was with about 15 $\mu$g of secretin. It appears that a higher dose of secretin would lead to a higher level of 7-MX in the urine.

Figure 7:
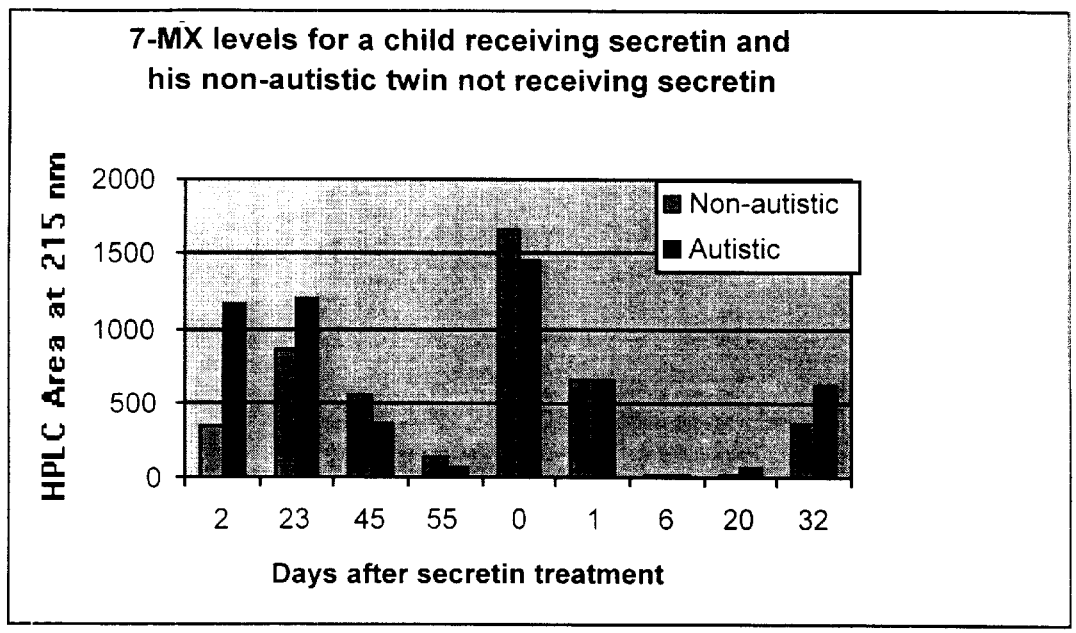
FIG. 7 is a graph showing the urine levels of 7-MX in an autistic child receiving secretin and in his normal brother who is not receiving secretin.

The time courses of another child's and his twin's 7-MX levels after treatment are shown in FIG. 7. One of the twins is autistic and the other is non-autistic. Secretin was not administered to the non-autistic twin. The level of 7-MX after the first secretin infusion in the autistic twin increased, and then decreased after about one week. For the second infusion, the 7-MX level on the day (labeled as day 0) right before secretin infusion was high. The 7-MX concentration of the non-autistic twin on the same day was at about the same level, indicating some dietary factors might have influenced the 7-MX levels on that day.

Example 5

Figure 8:
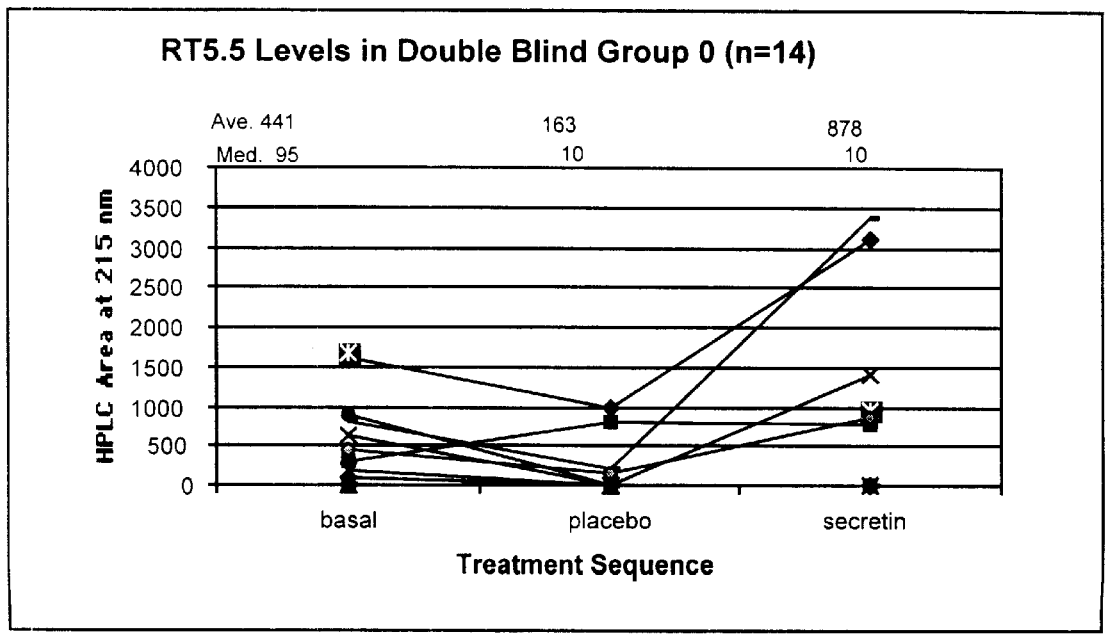
FIG. 8 is a graph showing the changes in urine levels of 7-MX in autistic individuals in a first double blind study group.
Figure 9:
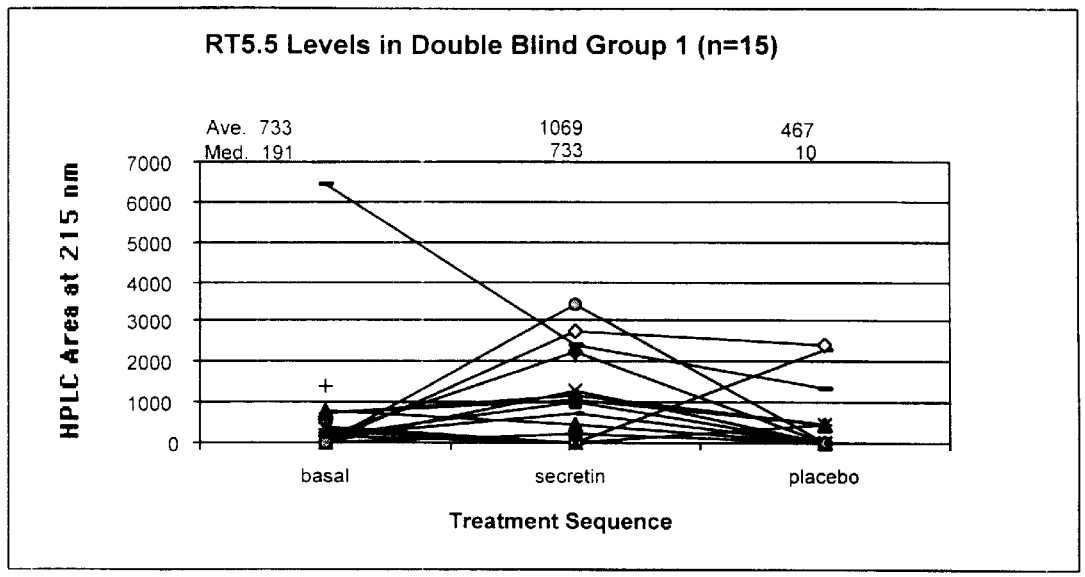
FIG. 9 is a graph showing the changes in urine levels of 7-MX in autistic individuals in a second double-blind study group.

Effect of Secretin Treatment of Urinary Production of 7-MX in Autistic Patients in Double Blind Study The urine samples of a double blind study on the effects of secretin on autistic children were available for further investigation on the changes of 7-MX after secretin treatment. Participants were divided into two groups. One group received secretin first, then placebo, and the other group received placebo first, then secretin. Three samples were collected for each subject: (i) basal urine, (ii) one week after secretin, (iii) one week after placebo. The changes of 7-MX level are shown in FIG. 8 (changes of 7-MX levels in double blind group "0") and FIG. 9 (changes of 7-MX in double blind group "1") for the two groups of patients. In both groups, the level of 7-MX after secretin treatment increased or stayed at the same level, but did not decrease. Only one subject in group 1 was an exception, where the basal 7-MX level was 10 times higher than the average. The time course study and the double blind study on the 7-MX levels in the urine of autistic children after secretin treatment clearly demonstrated that the infusion of secretin increased the excretion of 7-MX and other methylxanthines.

Example 6

Figure 10:
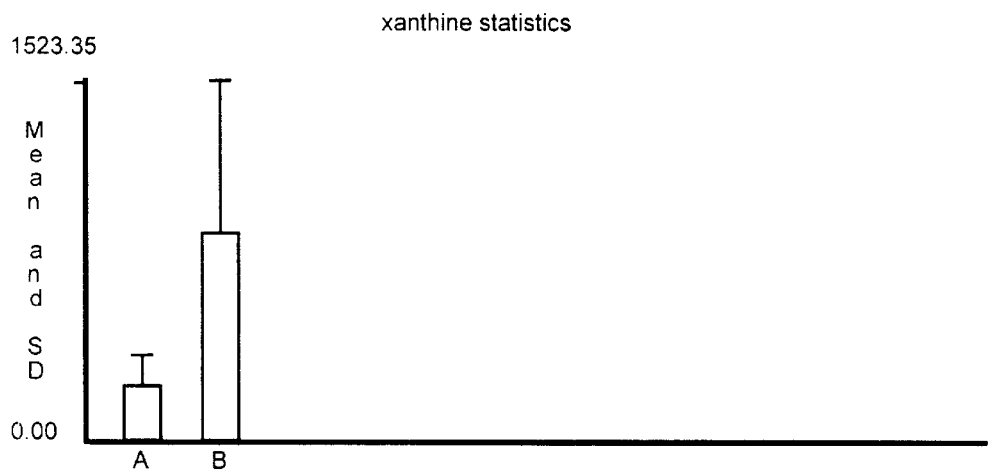
FIG. 10 is a graph showing mean xanthine levels in normal and autistic individuals.

Levels of Urinary Xanthines Differ Between Autistic and Non-Autistic Individuals The significant difference in the urine concentrations of methylxanthines between non-autistic children and autistic children lead to the investigation of the differences of other possible purine metabolites, such as xanthine. Xanthine can be identified by retention time and UV spectrum match with standard. The absorption area of xanthine at 215 nm was measured and the differences between the non-autistic and autistic group were studied. As shown in FIG. 10, the xanthine concentration in the autistic population was significantly higher than in the non-autistic population. In FIG. 10, A is the non-autistic group and B is the autistic group. The mean of the absorption area for the non-autistic group (n=9) is 242 and the mean for the autistic group (n=18) is 882. The P value of the two groups of data is 0.0069, considered very significant.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing an individual for an autistic disorder, the method comprising obtaining a sample of urine from the individual;
measuring a level of a methylxanthine (MX) in the urine sample; and
comparing the level to a normal control or to a threshold level;
wherein a level below the normal control or below a threshold level of about 5.3 micrograms of methylxanthine/ml of urine indicates a possibility of autistic disorder.

2. The method of claim 1, wherein an MX level below about 3.4 micrograms of methylxanthine/ml of urine indicates a strong likelihood that the individual has an autistic disorder.

3. The method of claim 1, wherein an MX level above about 5.3 micrograms of methylxanthine/ml of urine indicates a strong likelihood that the individual does not have an autistic disorder.

4. The method of claim 1, wherein the normal control is from an individual or group of individuals who are the same age as the individual being diagnosed, and who do not have any diagnosed symptoms of autistic disorder.

5. A method of treating an individual exhibiting one or more symptoms of autistic disorder, the method comprising administering to the individual an amount of a methylxanthine composition effective to inhibit one or more of the symptoms.

6. A method of claim 5, wherein an effective amount of the methylxanthine composition provides a urine concentration of at least about 5.0 micrograms of methylxanthine/ml of urine.

7. The method of claim 5, wherein the methylxanthine composition comprises 7-methylxanthine.

8. The method of claim 5, wherein the methylxanthine composition comprises a dimethylxanthine.

9. The method of claim 5, wherein the methylxanthine composition comprises a trimethylxanthine.

10. The method of claim 5, wherein the methylxanthine composition comprises one or more of caffeine, theobromine, and theophylline.

11. The method of claim 5, wherein the methylxanthine composition is administered orally.

12. The method of claim 5, wherein the methylxanthine composition is administered intravenously.

13. The method of claim 5, wherein the methylxanthine composition is administered at least once per day.

14. The method of claim 5, wherein the methylxanthine composition is administered at least once per week.

15. A method of diagnosing an individual for an autistic disorder, the method comprising obtaining a sample of urine from the individual;
measuring a level of a xanthine in the urine sample; and
comparing the level to a normal control;
wherein a level above the normal control indicates a likelihood that the individual has an autistic disorder.

16. The method of claim 15, wherein the level of xanthine is twice the level of the normal control.

17. The method of claim 15, wherein the level of xanthine is three times the level of the normal control.

18. The method of claim 15, wherein the normal control is from an individual or group of individuals who are the same age as the individual being diagnosed, and who do not have any diagnosed symptoms of autistic disorder.

* * * * *